(12) United States Patent
Holladay et al.

(10) Patent No.: US 9,012,699 B2
(45) Date of Patent: Apr. 21, 2015

(54) CHEMICAL PRODUCTION PROCESSES AND SYSTEMS

(71) Applicant: Battelle Memorial Institute, Richland, WA (US)

(72) Inventors: Johnathan E. Holladay, Richland, WA (US); Danielle S. Muzatko, Richland, WA (US); James F. White, Richland, WA (US); Alan H. Zacher, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

(21) Appl. No.: 14/274,193

(22) Filed: May 9, 2014

(65) Prior Publication Data

US 2014/0249335 A1    Sep. 4, 2014

Related U.S. Application Data

(60) Continuation of application No. 13/892,083, filed on May 10, 2013, now Pat. No. 8,754,266, which is a division of application No. 12/104,394, filed on Apr. 16, 2008, now abandoned.

(51) Int. Cl.
*C07C 27/00* (2006.01)
*C07C 29/132* (2006.01)
*C07C 29/60* (2006.01)

(52) U.S. Cl.
CPC ............... *C07C 29/132* (2013.01); *C07C 29/60* (2013.01)

(58) Field of Classification Search
None
See application file for complete search history.

(56) References Cited

U.S. PATENT DOCUMENTS

| | | | |
|---|---|---|---|
| 5,496,786 A | 3/1996 | Gubitosa et al. | |
| 5,543,379 A | 8/1996 | Gubitosa et al. | |
| 5,616,817 A | 4/1997 | Schuster et al. | |
| 6,291,725 B1 | 9/2001 | Chopade et al. | |
| 6,479,713 B1 | 11/2002 | Werpy et al. | |
| 6,841,085 B2 | 1/2005 | Werpy et al. | |
| 2003/0119952 A1* | 6/2003 | Werpy et al. | 524/115 |
| 2005/0244312 A1 | 11/2005 | Suppes et al. | |
| 2008/0025903 A1 | 1/2008 | Cortright | |
| 2008/0228014 A1 | 9/2008 | Bloom | |
| 2009/0088317 A1 | 4/2009 | Frye et al. | |

FOREIGN PATENT DOCUMENTS

EP    0 523 014    1/1993

OTHER PUBLICATIONS

WO PCT/US2009/040551 IPRP, Oct. 19, 2010, Battelle Memorial Institute.
WO PCT/US2009/040551 Search Rep., Jul. 2, 2009, Battelle Memorial Institute.
WO PCT/US2009/040551 Written Opi., Jul. 2, 2009, Battelle Memorial Institute.

* cited by examiner

*Primary Examiner* — Sudhakar Katakam
(74) *Attorney, Agent, or Firm* — Wells St. John P.S.

(57) ABSTRACT

Hydrogenolysis systems are provided that can include a reactor housing an Ru-comprising hydrogenolysis catalyst and wherein the contents of the reactor is maintained at a neutral or acidic pH. Reactant reservoirs within the system can include a polyhydric alcohol compound and a base, wherein a weight ratio of the base to the compound is less than 0.05. Systems also include the product reservoir comprising a hydrogenolyzed polyhydric alcohol compound and salts of organic acids, and wherein the moles of base are substantially equivalent to the moles of salts or organic acids. Processes are provided that can include an Ru-comprising catalyst within a mixture having a neutral or acidic pH. A weight ratio of the base to the compound can be between 0.01 and 0.05 during exposing.

15 Claims, 8 Drawing Sheets

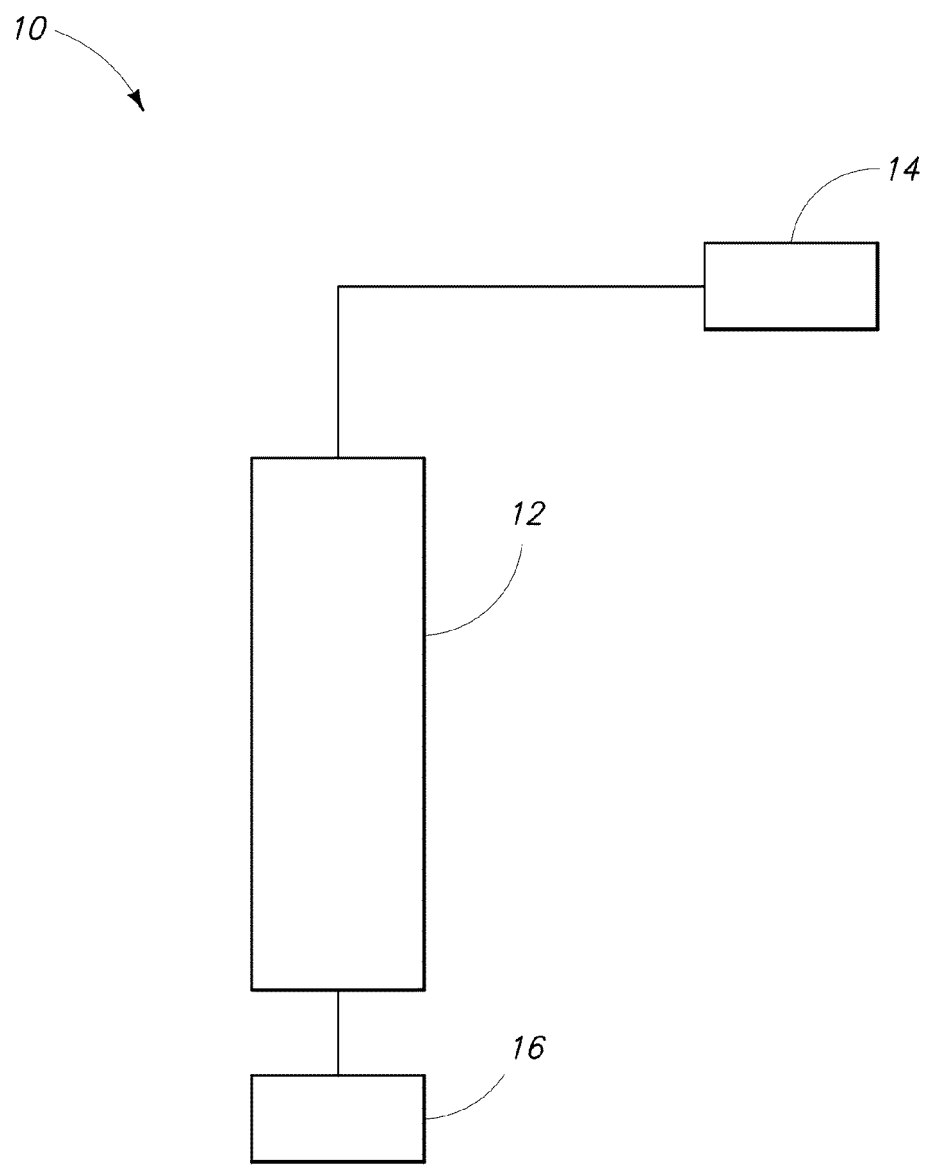

CHEMICAL PRODUCTION PROCESSES AND SYSTEMS

CROSS REFERENCE TO RELATED APPLICATION

This application is a continuation of U.S. patent application Ser. No. 13/892,083 which was filed May 10, 2013, entitled "Chemical Production Processes and Systems", which is a divisional of U.S. patent application Ser. No. 12/104,394 which was filed Apr. 16, 2008, entitled "Chemical Production Processes and Systems", the entirety of each of which is incorporated by reference herein.

STATEMENT AS TO RIGHTS TO INVENTIONS MADE UNDER FEDERALLY-SPONSORED RESEARCH AND DEVELOPMENT

This invention was made with Government support under Contract DE-ACO576RL01830 awarded by the U.S. Department of Energy. The Government has certain rights in the invention.

TECHNICAL FIELD

The present disclosure relates to chemical production processes and systems.

BACKGROUND

As the production of the multyhydric alcohol compounds has increased, conversion of these compounds to higher value compounds may be desired. For example, biodiesel fuel production methods can result in the production of by-product multihydric alcohol compounds such as glycerol. This glycerol can be converted to higher value polyols such as propylene glycol. This conversion may be desired to eliminate the glycerol by-product waste stream. The present disclosure provides chemical production systems and processes that allow for the conversion of multihydric alcohol compounds.

SUMMARY

Hydrogenolysis systems are provided that can include a reactant reservoir configured to contain a polyhydric alcohol compound and a reactor coupled to the reactant reservoir, the reactor housing an Ru-comprising hydrogenolysis catalyst and configured to expose the polyhydric alcohol compound to the catalyst, wherein the contents of the reactor is maintained at a neutral or acidic pH during the exposing.

Hydrogenolysis reactors are provided that contain a mixture comprising a polyhydric alcohol compound and an Ru-composition, wherein a pH of the mixture is neutral or acidic.

Hydrogenolysis processes are provided that can include exposing a polyhydric alcohol compound to an Ru-comprising catalyst to form a mixture, with the mixture having a neutral or acidic pH.

Processes for hydrogenolysing polyhydric alcohol compounds also include exposing a reactant mixture to an Ru-comprising catalyst, and while exposing the mixture to the catalyst, maintaining the contents of the reactor at a neutral or acidic pH. Processes also include providing a reactant mixture comprising a polyhydric alcohol compound and a base, wherein a weight ratio of the base to the compound is between 0.01 and 0.05, and exposing the mixture to a catalyst to at least partially hydrogenolyze a portion of the polyhydric alcohol compound.

Hydrogenolysis systems are provided that include a reactant reservoir coupled to a reactor, the reservoir configured to confine a reactant mixture, the reactant mixture comprising a polyhydric alcohol compound and a base, wherein a weight ratio of the base to the compound to is less than 0.05. Systems also include a reactor coupled to both a reactant reservoir and a product reservoir, a reactant mixture within the reactant reservoir, the reactant mixture comprising a polyhydric alcohol compound and a base, a product mixture within the product reservoir, the product reservoir comprising a hydrogenolyzed polyhydric alcohol compound and salts of organic acids, and wherein the moles of base are substantially equivalent to the moles of salts or organic acids.

BRIEF DESCRIPTION OF THE DRAWINGS

Embodiments of the disclosure are described below with reference to the following accompanying drawings.

FIG. 8 is a chemical production system according to an embodiment of the disclosure.

DESCRIPTION

This disclosure is submitted in furtherance of the constitutional purposes of the U.S. Patent Laws "to promote the progress of science and useful arts" (Article 1, Section 8).

Figure 1:
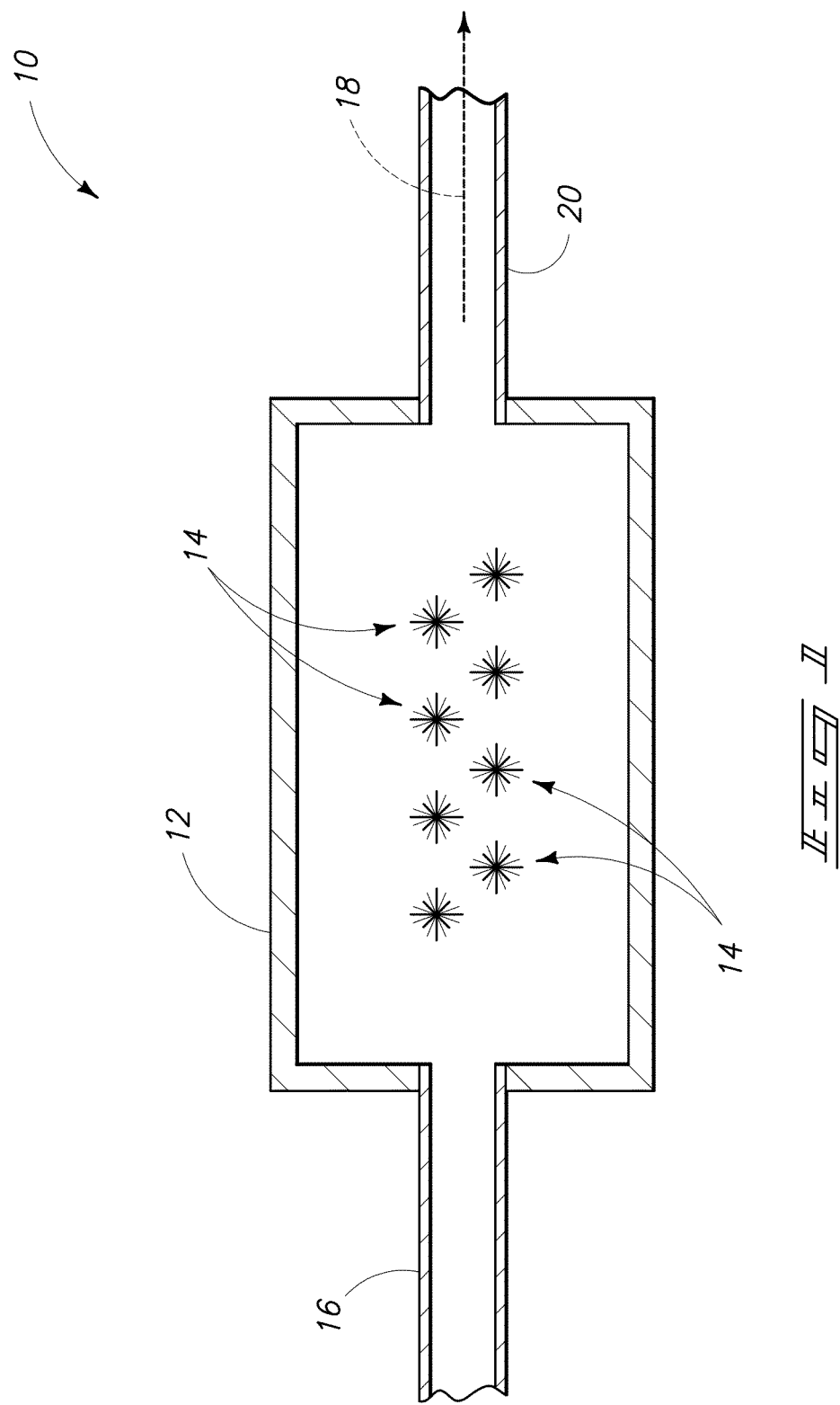
FIG. 1 is a portion of a chemical production system according to an embodiment of the disclosure.

Chemical production processes and systems are described with reference to FIGS. 1-8. Referring first to FIG. 1, a portion of a chemical production system 10 is shown that includes a reactor 12 housing a catalyst 14. Reactor 12 can be configured to be in fluid communication with a reactant stream 16 and a product stream 18. Reactor 12 within system 10 can be configured as an in-line reactor, but the present disclosure is not limited thereto. For example, other reactors can be utilized within system 10. The chemical processes can be facilitated in any reactor suitable for use under the desired conditions of temperature, pressure, solvent, and contact time. Examples reactors include but are not limited to: trickle bed, bubble column reactors, and continuous stirred tanks.

Reactant stream 16 coupled to reactor 12 can be received from a reservoir configured to contain a polyhydric alcohol compound. This polyhydric alcohol compound can be included in an aqueous solution containing as much as 90% water, for example. According to example implementations, reactant stream 16 can contain as much as 55% water and/or about 45% polyhydric alcohol compound. According to other implementations, stream 16 can contain between 20% and 40% polyhydric compound and a base. The base can be about 2% of the stream. Example embodiments of the process provide for the stream to have weight ratio of base to polyhydric compound. The weight ratio can be less than 0.05 or between 0.01 and 0.05 or between 0.025 and 0.05 or from 0.01 to 0.025. Reactant stream 16 does not contain a basic compound according to example implementations.

According to example implementations the reactant stream, the reactor contents, and/or the product stream as well as reservoirs associated with the reactant and/or product streams may be maintained at neutral or acidic pH. Neutral can be a system condition that can be characterized by the apparent concentration of $H^+$ being substantially equal to the apparent concentration of $OH^-$ in the system. Acidic can be a system condition that can be characterized by the apparent concentration of $H^+$ being greater than the apparent concentration of $OH^-$ in the system. Basic can be a system condition that can be characterized by the apparent concentration of $H^+$ being lesser than the apparent concentration of $OH^-$ in system.

For the purposes of determining these system characteristics, it is understood that for many systems, a pH value of 7.0 may not represent a neutral solution because pH value can vary based on the temperature of the solution, solvent effects of compounds in the solution, and relative ion activity of participating compounds, for example. However, substantially water containing systems of the disclosure can have a pH of reactant stream 16 can be less than or equal to 7.0. Other systems, substantially organic systems for example, such as high polyhydric alcohol compound systems may be considered neutral while having pH measurements above 7.0.

According to example implementations, the polyhydric alcohol compound can include n hydroxyl groups, with n being from 2 to 6 hydroxyl groups or from 2 to 3 hydroxyl groups. The polyhydric alcohol compound can be an oxygen containing organic compound such as a C-3 triol, for example. The polyhydric alcohol compounds can also include but are not limited to glycerol and/or sorbitol.

Reactant stream 16 can include a feedstock for the system. Such feedstocks can include but are not limited to sugars, sugar alcohols, glycerol, lactate or lactic acid. Sugars can include the sugars containing 6 carbon chains, such as glucose, galactose, maltose, lactose, sucrose, allose, altrose, mannose, gulose, idose, and talose (referred to herein as "6-carbon sugars"). Another group of sugars are the sugars containing 5 carbon chains, such as ribose, arabinose, xylose, and lyxose (referred to herein as "5-carbon sugars"). Sugar alcohols can include xylitol and or sorbitol, or the like, for example.

The feedstocks may be pure materials, purified mixtures or raw materials such as fermentation broth. Some feedstocks are commercially available. Some feedstocks could be obtained as side-products of other processes such as corn processing. Indeed, another advantage of the present invention is that, in some embodiments, the process can use materials that would otherwise be disposed as waste. The feedstocks can also be intermediates that are formed as part of a larger process or in the same process (such as sugar alcohols produced in the initial stage of hydrogenating a sugar). For some bio-based materials, it may be desirable to filter the materials and/or pass them through an ion exchange column or columns.

The feedstocks can include water or a nonaqueous solvent. Nonaqueous solvents can include methanol, ethanol, ethylene glycol, propylene glycol, n-propanol and i-propanol. Water may be desired because of its nontoxicity and prevalence in fermentation processes. The inventive processes have broad applicability, and, in some embodiments, the feedstock may include proteins and other materials. Feedstocks contain 20 to 60 wt % of reactants with the balance substantially composed of solvent.

Reactant stream 16 can include a reducing agent, for example, $H_2$. According to example implementations, a mole percent of the reducing agent to the polyhydric alcohol compound within reactant stream 16 can be at least about 35% of the polyhydric compound. Reactant stream 16 can be in fluid communication with reactor 12, and thereby reactant stream 16 can be exposed to catalyst 14 within reactor 12. While represented as a single conduit, reactant stream 16 can be configured as multiple conduits all in fluid communication with reactor 12. For example, each of the above described example components of reactant stream 16 (i.e., polyhydric alcohol compound, water, and/or reducing agent) may be provided to reactor 12 via its own conduit and/or in combination with other components from separate conduits.

Catalyst 14 within reactor 12 can be a hydrogenolysis catalyst. According to example embodiments, this catalyst can comprise Ru. Catalyst 14 can also comprise one or more of Ru, Zn, Cd, S, Te, Cu, Re, and Sn. Catalyst 14 can also comprise carbon, for example. Within reactor 12, catalyst 14 can be considered the solid phase and reactant stream 16 can be considered the liquid phase as a combination within the reactor. The solid phase can comprise the catalyst and the liquid phase can comprise the reactant. Reactant stream 16 can constitute the majority of the liquid phase within reactor 12, for example. The pH of the liquid phase can be less than 7.0 and the solid phase within this reactor can comprise one or more of Ru, Zn, Cd, S, Te, Cu, Re, and Sn.

According to example implementations, a solid phase within reactor 12 can include an Ru-composition. This Ru-composition can be promoted with one or more of Zn, Zu, Cd, S, Te, Cu, and/or Sn. This Ru-composition can include carbon as well. As an example, the Ru-composition can include at least about 5% (wt./wt.) Ru. The Ru-composition can also comprise from about 0.1% (wt./wt.) to about 1% (wt./wt.) promoters such as those described above. System 10 can be configured to expose reactant mixture 16 to catalyst 14 while maintaining a pH of the contents of reactor 12 below 7.0.

Catalysts are preferably made by incipient wetness impregnation techniques. A porous support may be purchased or prepared by known methods. A catalytic metal precursor is prepared or obtained. The precursor may be prepared, for example, by dissolving a metal compound in water or acid or purchasing a precursor in solution. The precursor may be in the form of a cation or an anion. A typical precursor for nickel may be nickel nitrate dissolved in water. A typical precursor for ruthenium may be ruthenium chloride. A typical precursor for rhenium may be perrhenic acid. Each of the precursor materials may be in liquid or solid form; these particles may also contain other components such as halides, cations, anions etc. In some embodiments, organic solvents may be avoided and the precursor impregnation solution can be prepared only in water. Conditions for preparing precursor solutions can depend on the type of metal and available ligands. In the case of a particulate support, such as activated carbon powders, the support and precursor composition can be mixed in a suspension. The support may not be coated by a vapor-deposited layer, and a method of making the catalyst may not have any vapor deposition step. A catalyst metal can be deposited subsequent to, or simultaneous with, the deposition of a metal oxide. Catalyst metal components can be impregnated into the support in a single-step, or by multi-step impregnation processes. According to one implemented method, the precursor for the catalyst component can be prepared in a single solution that is equivalent in volume to the measured amount of solvent that the porous support will uptake to fill all of the pore volume. This solution can be added to the dry support such that it is absorbed by the support and fills available pore volume. The support can then be vacuum dried in order to remove the solvent and leave the catalytic metal precursor to coat the surface of the support. Subsequent reduction can reduce the catalytic material to its metallic state or another oxidation state and may disassociate the metal from its anion or cation used to make the metal soluble. The catalyst can be reduced prior to use.

According to example embodiments, catalyst 14 can comprise one or both of Ni and Re. Via conduit 16, catalyst 14 can be exposed to a reducing agent. Example reducing agents include $H_2$. Catalyst 14 can be exposed to this reducing agent in the absence of polyhydric alcohol compounds such as glycerol. According to example implementations, the catalyst can be exposed to this reducing agent while maintaining a temperature of the catalyst within reservoir 14 below about 350° C. Where the catalyst comprises Ni and/or Re, the temperature of the catalyst can be maintained below 290° C. during the exposing. According to example implementations, the catalyst can comprise at least about 5% (wt./wt.) Ni. The remainder of the catalyst can be provided in a solid form on a support material that is selected to resist degradation under intended reaction conditions, for example. Such support materials may include high surface area oxide supports. Carbon, zirconium and titanium (especially in the rutile form) may be preferred because of their stability in hydrothermal conditions (aqueous solutions at above 100° C. and one atmosphere pressure). Supports can also be formed of mixed or layered materials. For example, in some preferred embodiments, the support is carbon with a surface layer of zirconia or zirconium mixed with catalyst metals. Of this support material, according to example implementations, 0.7% (wt./wt.) Re may be a part thereof. According to example implementations, the catalyst can include from between about 0.7% (wt./wt.) to about 2.5% (wt./wt.) Re.

According to example embodiments, catalyst preparation can include exposing catalyst 14 to a reducing atmosphere while maintaining the catalyst at a temperature of from between 265° C. and 320° C. The catalyst may then be passivated via exposure to the atmosphere, such exposure taking place, for example, during transfer of catalyst from reduction apparatus to reactor apparatus. Catalyst 14 can then be depassivated in the presence of a reducing agent while maintaining the catalyst at a temperature of less than 320° C. According to example implementations, where the catalyst comprises one or both of Ni and Re, during the exposing of the catalyst to a reducing atmosphere, the catalyst can be maintained at a temperature of from about 290° C. to about 320° C. The depassivating of the catalyst can include elevating the catalyst temperature from a first temperature to a temperature of less than 320° C. This elevation can take place at a rate less than about 2° C. per minute and/or at a rate of less than about 1.5° C. per minute. The reducing atmosphere or agent during this elevating can include one or both of $H_2$ and/or $N_2$. According to example implementations, the reducing agent can be at least about 5% (v/v) $H_2$.

According to other embodiments, the catalyst can comprise one or both of Co, Pd, and/or Re. In this catalyst system, the depassivating can include elevating the catalyst temperature from a first temperature to a temperature of less than 210° C. This elevating of this catalyst can include increasing the temperature at a rate of less than 1.5° C. per minute to a temperature less than 210° C.

According to example implementations, the exposing of the catalyst to a reducing agent can include elevating the temperature from a first temperature, such as ambient temperature, to at least about 210° C. at a rate of less than about 1.5° C. per minute. According to other implementations, the exposing can include elevating the temperature of the catalyst from a first temperature to a temperature of at least about 290° C. at a rate of less than about 1.5° C. per minute. The catalyst can be maintained at temperatures from about 265° C. to about 290° C. for hours at a time.

According to other example implementations, a catalyst can comprise one or more of Co, Pd, and Re. Within reservoir 12, this catalyst can be maintained from between about 260° C. and about 350° C. while exposing the catalyst to the reducing agent. According to other implementations, the temperature of the catalyst can be maintained between about 290° C. and about 350° C. In these systems, for example, the reducing agent can include $H_2$ in a relative inert such as nitrogen, and the reducing agent can comprise at least about 4% (v/v) $H_2$.

Catalyst 14 can be a previously activated catalyst that has subsequently become passivated, and this passivated catalyst can be provided to within reservoir 12 acting as a reactor, for example. According to example implementations, the passivated catalyst can be exposed to a reducing agent while maintaining the catalyst at a temperature of less than about 290° C.

During the exposing of reactant stream 16 to catalyst 14, reactor 12 can be maintained at a temperature of at least 190° C. and/or pressure of at least about 1200 psi.

In accordance with an example, glycerol hydrogenolysis can be performed using the systems described herein. Promoted Ru-composition catalysts can be prepared on Carbon and promoted with the promoters being one or more of Zn, Au, Cd, Se, Te, Cu and Sn. Catalysts can be prepared as 5% (wt./wt.) Ru with 0.1, 0.5 and 1% (wt./wt.) promoter. The support for the catalyst can be Norit ROX 0.8 carbon extrudate. Ni—Re and Ni—Fe based catalysts can also be utilized. The reactor feed can be of 10% (wt./wt.) glycerol in water. Base can be excluded from the reactor feed. Reactions can be performed under batch conditions at 200° C., under 1200 psi hydrogen with a stir rate of 850 rpm for 4 h. Catalyst compositions such as 5% Ru-1% Cd on C can provide 63% (64%) conversion, with a propylene glycol selectivity of 72% (64%) and mol balance of 86% (82%) (data in parentheses represent data from the catalyst duplicate runs). Zn catalyst systems such as 5% Ru-1% Zn on C can provide a 66% conversion with 34% selectivity and 61% mass balance. Table 1 below provides example data that may be acquired utilizing systems and processes of the present disclosure.

TABLE 1

| Neutral Hydrogenolysis | | | |
|---|---|---|---|
| | A | B | C |
| System Conditions F76 5% Ru + 1% Cd, 58959-85-1 | | | |
| Hours on stream | | 216:28:00 | 404:38:00 |
| Cat. Bed Temp (C. °) | 190 | 190 | 210 |
| System Pressure | 1200 | 1200 | 1200 |
| Liq. Feed Rate (ml/hr) | 50 | 25 | 25 |
| Glycerol Feed Concentration (wt %) | 44.95 | 44.95 | 44.95 |
| Glycerol Source | ADM | ADM | ADM |
| NaOH Feed Concentration (wt %) | 0.00 | 00.00 | 0.00 |
| H2/Glycerol Molar Feed Ratio | 5 | 5 | 5 |
| H2 Flow Rate (SCCM) | 252 | 252 | 454 |
| % Wt. Recovery | | 92.12 | 97.76 |

TABLE 1-continued

Neutral Hydrogenolysis

|  | A | B | C |
|---|---|---|---|
| % Carbon Recovery |  | 98.67 | 100.55 |
| Glycerol Conversion (By Difference) |  | 0.13 | 0.31 |
| LHSV (cc feed/cc cat/h) |  | 0.83 | 0.83 |
| WHSV (g/gly/g cat/h) |  | 0.85 | 0.85 |
| Space Time Yield (g PG/cc cat/h) |  | 0.04 | 0.11 |
| Selectivities |  |  |  |
| PG C Molar Selectivity |  | 0.990 | 0.991 |
| Lactate C. Molar Selectivity |  | 0.000 | 0.000 |
| EG C Molar Selectivity |  | 0.010 | 0.009 |
| Methanol C. molar Selectivity |  | 0.000 | 0.000 |
| Ethanol C. Molar Selectivity |  | 0.000 | 0.000 |
| Propaol (1&2) C Molar Selectivity |  | 0.0000 | 0.00000 |
| Summary |  |  |  |
| Rec. Run# |  | F76-6 | F76-11 |
| Hours on Stream: |  | 216:28:00 | 404:38:00 |
| Glycerol Conversion (By Difference) |  | 0.133 | 0.311 |
| PG C Molar Selectivity |  | 0.990 | 0.991 |
| Lactate C Molar Selectivity |  | 0.000 | 0.000 |
| EG C Molar Selectivity |  | 0.010 | 0.009 |
| Methanol C Molar Selectivity |  | 0.000 | 0.000 |
| Ethanol C. Molar Selectvity |  | 0.000 | 0.000 |
| Propanol (1&2) C Molar Selectivity |  | 0.00000 | 0.00000 |
| Product Solution pH |  | 0.00 | 0.00 |

Within the system described in FIG. 1, the reactant stream 16 can confine a reactant mixture. This mixture can include the polyhydric alcohol compound and a base. The base within this mixture can include less than 2.1% (wt./wt.) of the mixture. According to example configurations, this reactant mixture can comprise less than about 40% (wt./wt.) of the polyhydric alcohol compound. As implemented utilizing these base concentrations within the reactant mixture, the catayst can comprise one or more of Re, Co, Pd, and/or Ni. According to example implementations, the catalyst can comprise one or more of Re, Pd, and Co. With these implementations, the catalyst can comprise at least about 2.5% (wt./wt.) Co. The catalyst can also comprise at least about 0.5% (wt./wt.) Pd. The catalyst can also comprise at least about 2.5% (wt./wt.) Re.

Under these reactant mixture conditions, for example, the reactor can be configured to maintain the catalyst temperature between from about 180° C. to 210° C.

According to other implementations, the catalyst can comprise Re and Ni. In these catalyst systems, the catalyst can comprise at least about 1% (wt./wt.) Re. The catalyst can also comprise at least about 5% (wt./wt.) Ni.

According to example implementations, a hydrogenolysis process can be performed utilizing this system by providing a reactant mixture comprising a polyhydric alcohol compound and a base, with the base comprising less than about 2.1% (wt./wt.) of the reactant mixture. The reactant mixture can be exposed to a catalyst to at least partially hydrogenolyze a portion of the polyhydric alcohol compound. According to example implementations, the base within the reaction mixture can comprise from about 0.5% (wt./wt.) to about 2.1% (wt./wt.) of the reactant mixture or be less than about 1% (wt./wt.) of the reactant mixture. According to other implementations, the base can comprise from about 0.5% (wt./wt.) to about 1% (wt./wt.) of the reactant mixture. According to other embodiments, the process can include, prior to exposing the mixture to a catalyst, depassivating the catalyst in the presence of a reducing atmosphere at a temperature of less than about 210° C.

EXAMPLE 1

Co/Pd/Re Catalyst

Thirty cubic centimeters of reduced/passivated catalyst can be packed into a down-flow trickle bed reactor. The catalyst can be activated by raising the temperature of the reactor 2° C./min to 325° C. During the ramp a 10% $H_2$ in $N_2$ gas mixture can be passed over the catalyst at 250 sccm. Once the temperature is reached the $H_2$ concentration in the gas mixture can be increased to 100% and the temperature can be held for 2 h. The reactor temperature can be lowered to 190° C., the gas flow rate can be increased to 450 sccm and the pressure raised to 1200 psig. Glycerol feed can be started at a rate of 1.7 LHSV (40 mL/min). The initial glycerol feed used can be of 40% (wt./wt.) glycerol and 2.1% (wt./wt.) NaOH in water. The base concentration in the feed can be reduced to 1% (wt./wt.). Three temperatures (200, 190, 180° C.) and three space velocities (1.7, 1.2, 0.8 $h^{-1}$) can be run using these reactant mixture conditions. The base concentration can then be lowered to 0.5% (wt./wt.) and the tests described above repeated. Results are shown in Tables 2 and 3 with data represented graphically in FIGS. 2-4.

EXAMPLE 2

Ni/Re Catalyst

Thirty cubic centimeters of reduced/passivated catalyst can be packed into a down-flow trickle bed reactor. The catalyst can be activated by raising the temperature of the reactor 1.5° C./min to 210° C. During the ramp a 10% $H_2$ in $N_2$ gas mixture can be passed over the catalyst at 250 sccm. Once the temperature is reached, the $H_2$ concentration in the gas mixture can be increased to 100% and the temperature can be held for 2 h. The reactor temperature can be lowered to 190° C. and the gas flow rate can be increased to 450 sccm and the pressure raised to 1200 psig. Glycerol feed can be started at a rate of 1.7 LHSV (40 mL/min) with the initial glycerol feed including of 40% (wt./wt.) glycerol and 2.1% (wt./wt.) NaOH in water. The base concentration in the feed can be reduced to 1% (wt./wt.). Three temperatures (200, 190, 180° C.) and three space velocities (1.7, 1.2, 0.8 $h^{-1}$) can be evaluated using the same catalyst/reactant mixture system. The base concentration can then be lowered to 0.5% (wt./wt.) and the tests described above repeated. Results are shown in Tables 4 and 5 with data represented graphically in FIGS. 5-6.

EXAMPLE 3

4.9% Ni, 0.7% Re

Thirty cubic centimeters of reduced/passivated catalyst (4.9% Ni, 0.7% Re) can be packed into a down-flow trickle bed reactor. The reactor temperature, the gas flow rate, the pressure, the Glycerol feed, etc. as well as results are shown in Table 6 with data represented graphically in FIG. 7.

TABLE 2

Data at 1% NaOH

| | F59-28 | F59-29 | F59-30 | F59-30B | F59-31 | F59-32 | F59-33 | F59-34 |
|---|---|---|---|---|---|---|---|---|
| System Conditions | | | | | | | | |
| Hours on stream | 1050.4 | 1120.9 | 1169.6 | 1174.9 | 1193.1 | 1217.4 | 1267.3 | 1279.8 |
| Hours on stream ADM Feed | <500 | | | | | | | |
| Cat. Bed Temp (° C.) | 190 | 190 | 180 | 180 | 190 | 180 | 180 | 190 |
| System Pressure | 1200 | 1200 | 1200 | 1200 | 1200 | 1200 | 1200 | 1200 |
| Liq. Feed Rate (ml/hr) | 50 | 50 | 25 | 25 | 35 | 50 | 35 | 25 |
| Glycerol Feed Conc. (wt %) | 37.11 | 39.08 | 39.08 | 39.08 | 39.08 | 39.08 | 40.03 | 40.03 |
| Glycerol Source | ADM-IE | Fisher | Fisher | Fisher | Fisher | Fisher | Fisher | Fisher |
| NaOH Feed Conc. (wt %) | 2.10 | 1.00 | 1.00 | 1.00 | 1.00 | 1.00 | 1.00 | 1.00 |
| H2/Glycerol Molar Feed Ratio | 5 | 5 | 5 | 5 | 5 | 5 | 5 | 5 |
| H2 Flow Rate (SCCM) | 454 | 454 | 227 | 227 | 318 | 454 | 318 | 227 |
| % Wt. Recovery | 99.21 | 98.26 | 91.58 | 98.38 | 98.13 | 97.56 | 94.59 | 99.22 |
| % Carbon Recovery | 98.86 | 96.78 | 92.08 | 98.65 | 94.43 | 98.76 | 94.50 | 96.92 |
| Glycerol Conversion (By Differ | 0.948 | 0.844 | 0.809 | 0.793 | 0.892 | 0.649 | 0.752 | 0.942 |
| Selectivities | | | | | | | | |
| PG C Molar Selectivity | 0.913 | 0.940 | 0.958 | 0.957 | 0.938 | 0.955 | 0.958 | 0.939 |
| Lactate C Molar Selectivity | 0.026 | 0.016 | 0.012 | 0.012 | 0.015 | 0.012 | 0.012 | 0.017 |
| EG C Molar Selectivity | 0.033 | 0.031 | 0.024 | 0.024 | 0.030 | 0.024 | 0.024 | 0.030 |
| Methanol C molar Selectivity | 0.018 | 0.009 | 0.006 | 0.006 | 0.011 | 0.004 | 0.005 | 0.010 |
| Ethanol C Molar Selectivity | 0.005 | 0.002 | 0.000 | 0.000 | 0.001 | 0.000 | 0.000 | 0.002 |
| Product Solution pH | 12.38 | 12.24 | 11.81 | 11.81 | 11.51 | 11.79 | 12.10 | 11.88 |

Liquid feed rate of 50 35 and 25 ml/h correspond to LHSV of 1.7, 1.2 and 0.8 $h^{-1}$.

TABLE 3

Data at 0.5% NaOH

| | F59-39 | F59-40 | F59-41 | F59-42 | F59-43 | F59-44 | F59-45 | F59-46 | F59-47 |
|---|---|---|---|---|---|---|---|---|---|
| System Conditions | | | | | | | | | |
| Hours on stream | 1529.4 | 1536.6 | 1557.1 | 1625.7 | 1648.9 | 1657.7 | 1699.3 | 1722.1 | 1793.7 |
| Hours on stream ADM Feed | | | | | | | | | |
| Cat. Bed Temp ° C. | 190 | 200 | 200 | 180 | 180 | 190 | 190 | 200 | 180 |
| System Pressure | 1200 | 1200 | 1200 | 1200 | 1200 | 1200 | 1200 | 1200 | 1200 |
| Liq. Feed Rate ml/hr | 50 | 25 | 50 | 25 | 50 | 25 | 35 | 35 | 35 |
| Glycerol Feed Conc. wt % | 39.287 | 39.287 | 39.287 | 39.287 | 39.287 | 39.287 | 39.287 | 39.237 | 39.237 |
| Glycerol Source | Fisher | Fisher | Fisher | Fisher | Fisher | Fisher | Fisher | Fisher | Fisher |
| NaOH Feed Conc. wt % | 0.5 | 0.5 | 0.5 | 0.5 | 0.5 | 0.5 | 0.5 | 0.5 | 0.5 |
| H2/Glycerol Molar Feed Ratio | 5 | 5 | 5 | 5 | 5 | 5 | 5 | 5 | 5 |
| H2 Flow Rate SCCM | 454 | 227 | 454 | 227 | 454 | 227 | 318 | 318 | 318 |
| Analytical | | | | | | | | | |
| % Wt. Recovery | 98.3 | 98.7 | 98.7 | 98.5 | 98.4 | 98.9 | 98.4 | 98.8 | 97.4 |
| % Carbon Recovery | 97.0 | 95.1 | 92.8 | 98.4 | 98.4 | 96.6 | 96.4 | 96.3 | 97.0 |
| Glycerol Conversion | 0.69 | 0.94 | 0.83 | 0.66 | 0.46 | 0.86 | 0.79 | 0.89 | 0.56 |
| Selectivities | | | | | | | | | |
| PG C Molar Selectivity | 0.951 | 0.933 | 0.927 | 0.945 | 0.965 | 0.949 | 0.969 | 0.929 | 0.963 |
| Lactate C Molar Selectivity | 0.013 | 0.018 | 0.019 | 0.011 | 0.010 | 0.014 | 0.013 | 0.018 | 0.011 |
| EG C Molar Selectivity | 0.028 | 0.033 | 0.034 | 0.021 | 0.020 | 0.027 | 0.003 | 0.034 | 0.021 |
| Methanol C molar Selectivity | 0.005 | 0.008 | 0.012 | 0.006 | 0.000 | 0.008 | 0.008 | 0.012 | 0.003 |
| Ethanol C Molar Selectivity | 0.000 | 0.0008 | 0.002 | 0.000 | 0.004 | 0.000 | 0.000 | 0.001 | 0.000 |
| Propanol (1&2) C Molar Selectivity | | | | | 0.0 | 0.0 | 0.0 | 0.0 | 0.0 |
| Summary info | | | | | | | | | |
| LHSV (h-1) | 1.667 | 0.833 | 1.667 | 0.833 | 1.667 | 0.833 | 1.167 | 1.167 | 1.167 |
| WHSV (h-1) | 1.609 | 0.805 | 1.609 | 0.805 | 1.609 | 0.805 | 1.127 | 1.125 | 1.125 |
| Space Time Yield (h-1) | 0.834 | 0.554 | 0.940 | 0.402 | 0.569 | 0.523 | 0.677 | 0.741 | 0.478 |
| Product Solution pH | 11.31 | 11.94 | 11.25 | 11.97 | 0.00 | 11.62 | 12.03 | 11.85 | 12.37 |

TABLE 4

Ni/Re 1% Base

| | F65-6 | F65-7 | F65-8 | F65-9 | F65-10 | F65-11 | F65-12 |
|---|---|---|---|---|---|---|---|
| System Conditions | | | | | | | |
| Hours on stream | 240.9 | 311.8 | 360.3 | 383.7 | 407.7 | 458.0 | 470.5 |
| Cat. Bed Temp (° C.) | 190 | 190 | 180 | 190 | 180 | 180 | 190 |
| System Pressure | 1200 | 1200 | 1200 | 1200 | 1200 | 1200 | 1200 |
| Liq. Feed Rate (ml/hr) | 50 | 50 | 25 | 35 | 50 | 35 | 25 |
| Glycerol Feed Concent. (wt %) | 40.20 | 39.27 | 39.27 | 39.27 | 39.27 | 38.51 | 38.51 |
| Glycerol Source | Fisher | Fisher | Fisher | Fisher | Fisher | Fisher | Fisher |
| NaOH Feed Concent. (wt %) | 2.10 | 1.00 | 1.00 | 1.00 | 1.00 | 1.00 | 1.00 |
| H2/Glycerol Molar Feed Ratio | 5 | 5 | 5 | 5 | 5 | 5 | 5 |
| H2 Flow Rate (SCCM) | 454 | 454 | 227 | 318 | 454 | 318 | 227 |
| % Wt. Recovery | 97.218 | 96.783 | 94.221 | 96.749 | 98.735 | 96.574 | 98.249 |
| % Carbon Recovery | 94.184 | 99.266 | 97.035 | 97.289 | 95.273 | 100.423 | 99.639 |
| Glycerol Conversion | 0.944 | 0.733 | 0.735 | 0.851 | 0.578 | 0.615 | 0.887 |
| Selectivities | | | | | | | |
| PG C Molar Selectivity | 0.904 | 0.933 | 0.962 | 0.929 | 0.965 | 0.963 | 0.943 |
| Lactate C Molar Selectivity | 0.026 | 0.016 | 0.010 | 0.015 | 0.010 | 0.010 | 0.014 |
| EG C Molar Selectivity | 0.034 | 0.031 | 0.023 | 0.032 | 0.024 | 0.023 | 0.030 |
| Methanol C molar Selectivity | 0.014 | 0.015 | 0.004 | 0.016 | 0.000 | 0.003 | 0.011 |
| Ethanol C Molar Selectivity | 0.008 | 0.003 | 0.000 | 0.003 | 0.000 | 0.000 | 0.001 |
| Product Solution pH | 12.29 | 12.37 | | 11.34 | 11.67 | 12.22 | 12.17 |

TABLE 5

Ni/Re Data at 0.5% NaOH Loading

| | F68-3 | F68-4 | F68-5 | F68-6 | F68-7 | F68-8 | F68-9 | F68-10 | F68-11 | F68-12 |
|---|---|---|---|---|---|---|---|---|---|---|
| System Conditions | | | | | | | | | | |
| Hours on stream | 136.9 | 184.8 | 256.6 | 264.4 | 284.1 | 305.0 | 312.0 | 335.5 | 474.2 | 498.2 |
| Cat. Bed Temp (° C.) | 190 | 190 | 200 | 190 | 200 | 180 | 180 | 200 | 180 | 190 |
| System Pressure | 1200 | 1200 | 1200 | 1200 | 1200 | 1200 | 1200 | 1200 | 1200 | 1200 |
| Liq. Feed Rate (ml/hr) | 50 | 50 | 25 | 25 | 50 | 50 | 35 | 35 | 25 | 35 |
| Glycerol Feed Concentration (wt %) | 38.01 | 39.24 | 39.24 | 39.24 | 39.24 | 39.24 | 39.24 | 39.24 | 39.24 | 39.24 |
| Glycerol Source | Fisher | Fisher | Fisher | Fisher | Fisher | Fisher | Fisher | Fisher | Fisher | Fisher |
| NaOH Feed Concentration (wt %) | 2.10 | 0.50 | 0.50 | 0.50 | 0.50 | 0.50 | 0.50 | 0.50 | 0.005 | 0.05 |
| H2/Glycerol Molar Feed Ratio | 5 | 5 | 5 | 5 | 5 | 5 | 5 | 5 | 5 | 5 |
| H2 Flow Rate (SCCM) | 454 | 454 | 252 | 252 | 454 | 454 | 318 | 318 | 225 | 318 |
| % Wt. Recovery | 99.264 | 96.221 | 95.522 | 97.169 | 96.363 | 96.754 | 97.329 | 98.121 | 95.066 | 95.797 |
| % Carbon Recovery | 98.461 | 94.191 | 95.698 | 95.668 | 115.012 | 96.666 | 94.731 | 95.715 | 96.889 | 98.994 |
| Glycerol Conversion (By Difference) | 0.90 | 0.66 | 0.91 | 0.81 | 0.77 | 0.45 | 0.54 | 0.85 | 0.63 | 0.73 |
| Selectivities | | | | | | | | | | |
| PG C Molar Selectivity | 0.905 | 0.939 | 0.924 | 0.945 | 0.926 | 0.962 | 0.960 | 0.924 | 0.960 | 0.947 |
| Lactate C Molar Selectivity | 0.030 | 0.017 | 0.017 | 0.014 | 0.015 | 0.013 | 0.013 | 0.018 | 0.012 | 0.014 |
| EG C Molar Selectivity | 0.033 | 0.027 | 0.034 | 0.028 | 0.034 | 0.021 | 0.022 | 0.034 | 0.022 | 0.028 |
| Methanol C molar Selectivity | 0.009 | 0.008 | 0.014 | 0.010 | 0.013 | 0.003 | 0.003 | 0.017 | 0.005 | 0.009 |
| Ethanol C Molar Selectivity | 0.008 | 0.001 | 0.003 | 0.001 | 0.002 | 0.000 | 0.000 | 0.002 | 0.000 | 0.000 |
| Propanol (1 & 2) C Molar Selectivity | 0.0050 | 0.0068 | 0.0052 | 0.0023 | 0.0046 | 0.0018 | 0.0020 | 0.0040 | 0.0040 | 0.0040 |
| Summary Info | | | | | | | | | | |
| LHSV (ml feed/ml cat/h) | 1.667 | 1.667 | 0.833 | 0.833 | 1.667 | 1.667 | 1.167 | 1.167 | 0.833 | 1.167 |
| WHSV (g gly/g cat/h) | 1.660 | 1.714 | 0.857 | 0.857 | 1.714 | 1.714 | 1.200 | 1.200 | 0.857 | 1.200 |
| STY (g PG/ml cat/h) | 0.341 | 0.340 | 0.241 | 0.220 | 0.516 | 0.243 | 0.200 | 0.317 | 0.175 | 0.288 |

TABLE 6

F64: 4.9% Ni, 0.7% Re; 190° C., 1200 psig H2, 40 wt % gly, 2.1% NaOH

| | F64-1G | F64-1 | F64-2G | F-64G3 | F64-4 | F64-5 | F64-6 | F64-7 | F64-8 | F64-9 | F64-10 | F64-11 | F64-12 | F64-13 |
|---|---|---|---|---|---|---|---|---|---|---|---|---|---|---|
| System Conditions | | | | | | | | | | | | | | |
| Hours on stream | 16.5 | 70.7 | 114.0 | 143.6 | 233.5 | 283.4 | 305.6 | 332.0 | 402.0 | 448.8 | 496.7 | 577.7 | 625.1 | 667.1 |
| Cat. Bed Temp (° C.) | 190 | 190 | 190 | 190 | 190 | 190 | 190 | 190 | 190 | 190 | 190 | 190 | 190 | 190 |
| System Pressure | 1200 | 1200 | 1240 | 1200 | 1200 | 1200 | 1200 | 1200 | 1200 | 1200 | 1200 | 1200 | 1200 | 1200 |
| Liq. Feed Rate (ml/hr) | 50 | 50 | 50 | 50 | 50 | 50 | 50 | 35 | 35 | 35 | 35 | 35 | 35 | 35 |
| Glycerol Feed Concentration (wt %) | 39.90 | 39.9 | 39.96 | 39.96 | 37.31 | 37.31 | 37.31 | 36.74 | 36.74 | 36.74 | 36.74 | 35.10 | 35.10 | 35.10 |
| Glycerol Source | Fisher | Fisher | Fisher | Fisher | ADM-3 | ADM-3 | ADM-3 | ADM-4A | ADM-4A | ADM-4A | ADM-4A | ADM-5A | ADM-5A | ADM-5A |
| NaOH Feed Concentration (wt %) | 2.10 | 2.10 | 2.10 | 2.10 | 2.10 | 2.10 | 2.10 | 2.10 | 2.10 | 2.10 | 2.10 | 2.10 | 2.10 | 2.10 |
| H2/Glycerol Molar Feed Ratio | 5 | 5 | 5 | 5 | 5 | 5 | 5 | 5 | 5 | 5 | 5 | 5 | 5 | 5 |
| H2 Flow Rate (SCCM) | 450 | 450 | 450 | 450 | 450 | 450 | 450 | 315 | 315 | 315 | 315 | 315 | 315 | 315 |
| % Wt. Recovery | 97.07 | 97.19 | 91.46 | 98.90 | 95.39 | 95.99 | 97.12 | 95.38 | 93.86 | 95.72 | 94.65 | 94.80 | 93.67 | 94.15 |
| Carbon Recovery | 88.59 | 95.75 | 87.46 | 95.15 | 99.10 | 96.24 | 97.55 | 96.24 | 94.31 | 95.19 | 93.49 | 94.55 | 92.90 | 93.30 |
| Glycerol Conversion (By Difference) | 0.89 | 0.86 | 0.86 | 0.85 | 0.81 | 0.81 | 0.81 | 0.88 | 0.88 | 0.88 | 0.88 | 0.88 | 0.87 | 0.88 |
| Selectivities | | | | | | | | | | | | | | |
| PG C Molar Selectivity | 0.92 | 0.93 | 0.93 | 0.93 | 0.92 | 0.93 | 0.93 | 0.93 | 0.93 | 0.93 | 0.93 | 0.93 | 0.94 | 0.93 |
| Lactate C Molar Selectivity | 0.02 | 0.02 | 0.02 | 0.02 | 0.02 | 0.02 | 0.02 | 0.02 | 0.02 | 0.02 | 0.02 | 0.02 | 0.02 | 0.02 |
| EG C Molar Selectivity | 0.04 | 0.03 | 0.03 | 0.04 | 0.03 | 0.03 | 0.03 | 0.03 | 0.03 | 0.03 | 0.03 | 0.03 | 0.03 | 0.03 |
| Methanol C molar Selectivity | 0.01 | 0.01 | 0.01 | 0.01 | 0.01 | 0.02 | 0.01 | 0.01 | 0.01 | 0.02 | 0.01 | 0.01 | 0.01 | 0.01 |
| Ethanol C Molar Selectivity | 0.01 | 0.00 | 0.00 | 0.00 | 0.00 | 0.00 | 0.00 | 0.00 | 0.00 | 0.00 | 0.00 | 0.00 | 0.00 | 0.00 |
| Product Solution PH | 12.54 | 11.88 | 12.72 | 12.18 | 11.92 | 12.54 | 12.93 | 13.15 | 13.06 | 13.22 | 12.78 | 13.29 | 11.85 | 11.99 |

Figure 2:
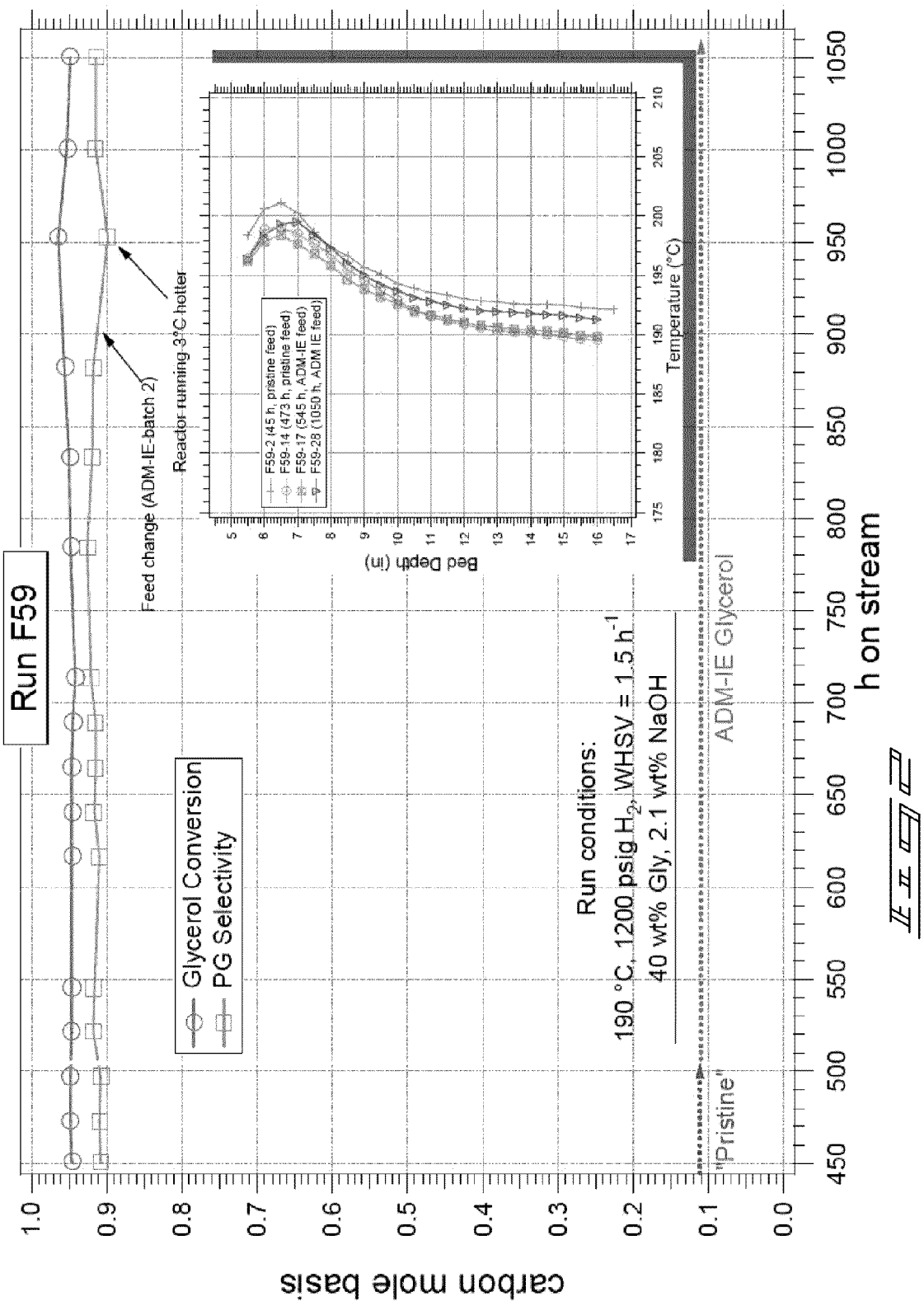
FIG. 2 is graphical representation of data acquired utilizing the processes and methods described according to an embodiment.
Figure 3:
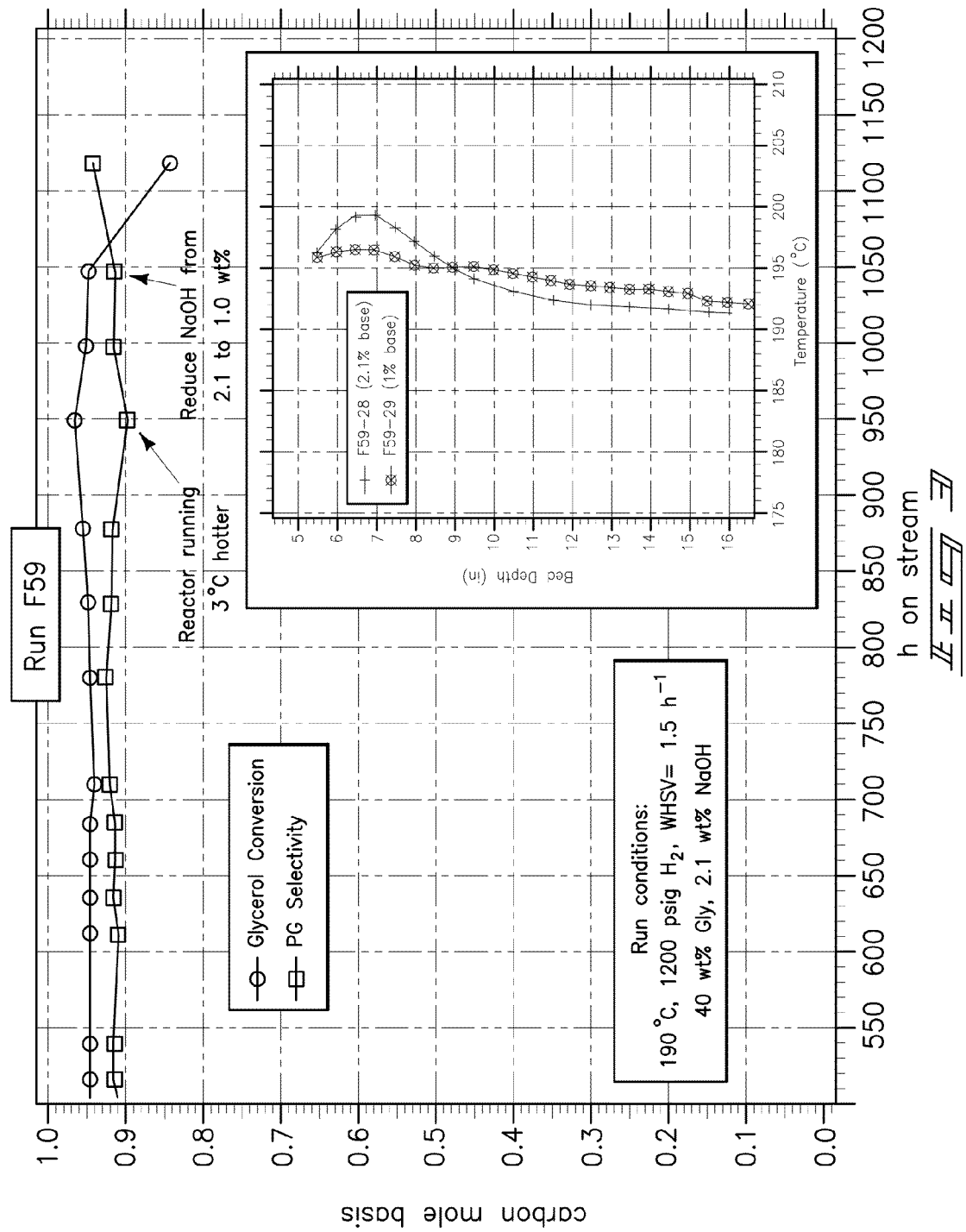
FIG. 3 is graphical representation of data acquired utilizing the processes and methods described according to an embodiment.
Figure 4:
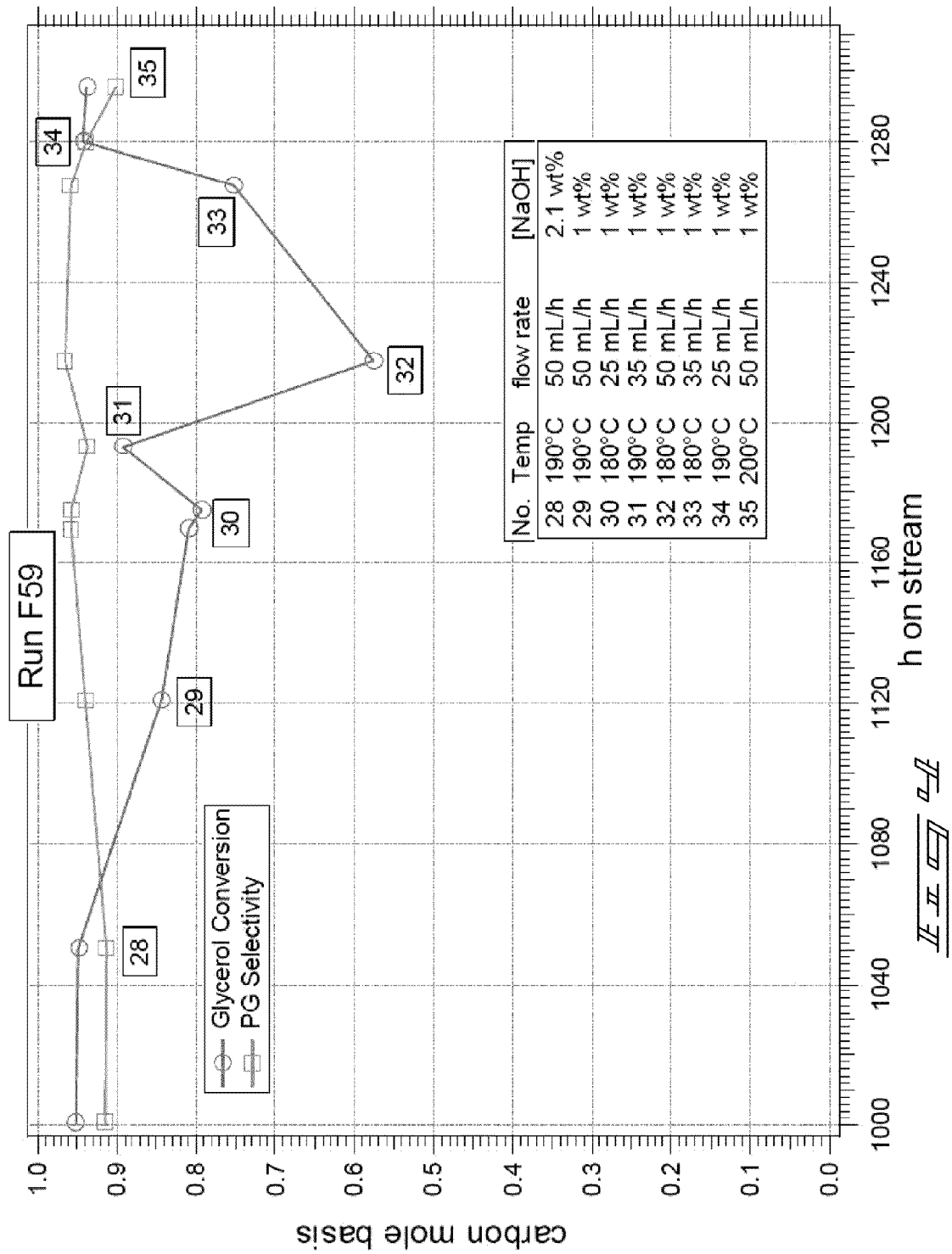
FIG. 4 is graphical representation of data acquired utilizing the processes and methods described according to an embodiment.
Figure 5:
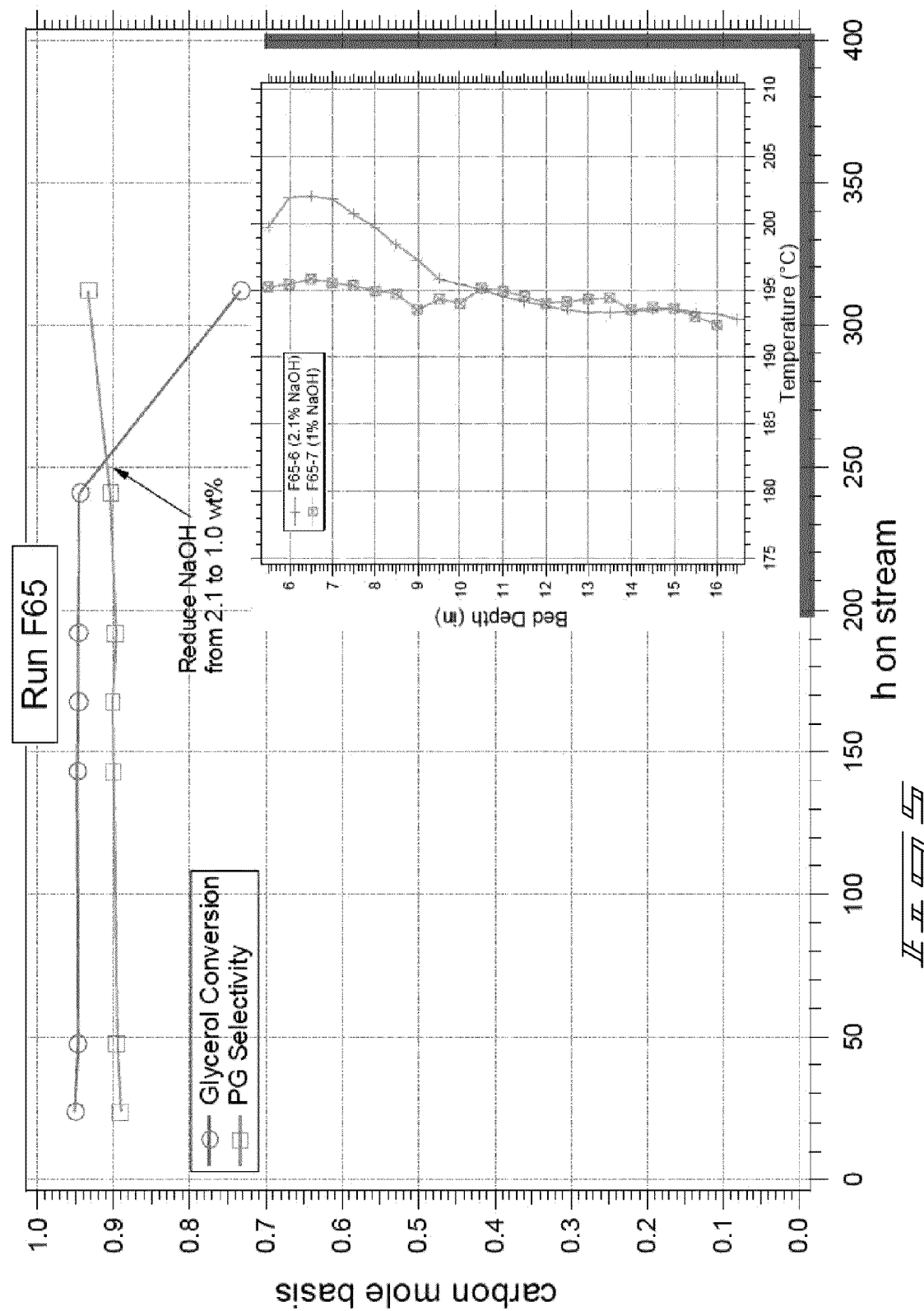
FIG. 5 is graphical representation of data acquired utilizing the processes and methods described according to an embodiment.
Figure 6:
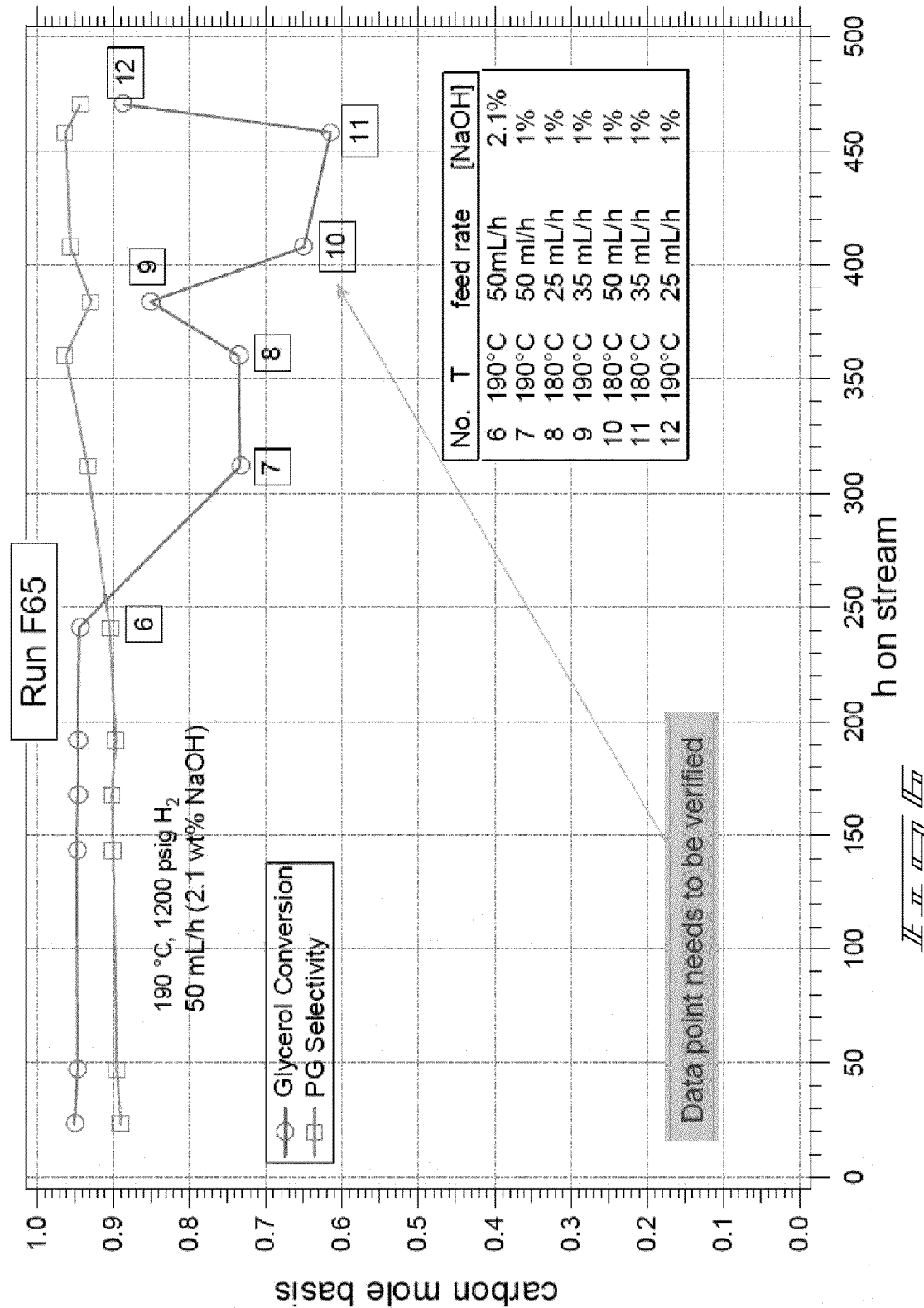
FIG. 6 is graphical representation of data acquired utilizing the processes and methods described according to an embodiment.
Figure 7:
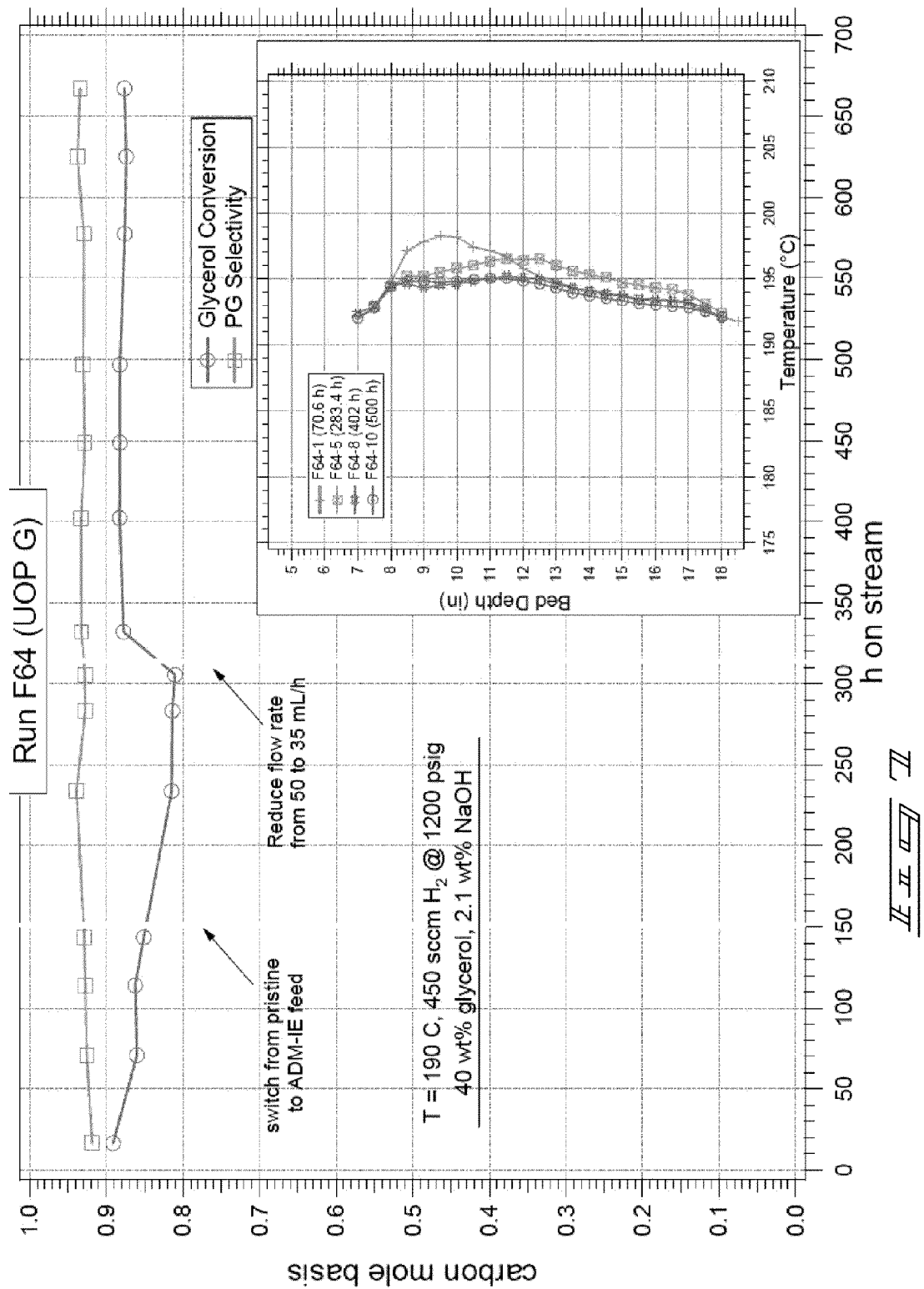
FIG. 7 is graphical representation of data acquired utilizing the processes and methods described according to an embodiment.

Referring to FIG. 2, as another example of a system, system 20 is presented with reactor 22 and reactant reservoir 24 coupled to product reservoir 16. System 20 is an example trickle down bed reactor for use in connection with the chemical processes. System 20, for example can have a reactant mixture within reactant reservoir 24, the reactant mixture can include a polyhydric alcohol compound and a base. During system utilization, a product mixture can be within product reservoir 16, the product reservoir can include a hydrogenolyzed polyhydric alcohol compound and salts of organic acids, for example. System 20 can be configured to provide that the carbon molar selectivity to organic acids and salts of organic acids is less than 2% and the carbon molar selectivity to hydrogenolyzed polyhydric alcohol compound is at least 30%.

As an example, the polyhydric alcohol compound can be glycerol and at least one of the salts of organic acids include lactate and the base comprises Na and/or K, such as NaOH or KOH. The mole ratio of lactate to base can be approximately 1 and/or a weight ratio of the base to the polyhydric alcohol compound within the reactant mixture is less than 0.05.

According to example implementations methods provide for the operation of a reactor for the hydrogenolysis of multihydric alcohol compounds at slightly basic, neutral or acidic pH in order to disfavor the formation of salts of organic acids normally formed under basic conditions. Example implementations can achieve high selectivity to desired compounds, for example in the conversion of glycerol to propylene glycol, by nearly eliminating the formation of lactate salt, formate salt, glycerate salt, and glycolate salt that are known byproducts.

In accordance with example implementations, the present disclosure provide methods of performing the multiple reaction steps of the prior art into a single reaction by the application of a catalyst that is active under selected conditions for multiple reactions.

This has broader application, in that the resultant product stream from such an application to multihydric alcohol hydrogenolysis would contain virtually insignificant amounts of the organic acids or organic acid salts that have been reported in prior literature. This application would be expanded not only to glycerol as a feedstock, but it would be expected to shut down the formation of the acid salt byproducts from the conversion of other compounds such as sorbitol, xylitol, and arabitol to higher value polyols. This application would also be expanded to include other catalysts that are found to be both active and stable under neutral and acidic conditions during the course of this reaction.

As an example and with reference to Table 7 below. Under the low to no-base conditions hydrogenolysis can be efficiently realized in that organic acid salt byproducts can be substantially eliminated below analytical detection after the system utilizes neutral feedstock having previously run on feed containing sodium hydroxide as a base. Conversion 31% with little to no detectable selectivity to lactate, compared to the 1% to 4% carbon molar selectivity to lactate reported in the samples of reaction product generated from feed that has substantial amounts of base.

Hydrogenolysis product streams can have little to undetected levels of organic acid or organic acid salt byproducts due to adjustments of the pH from lower than normally reported all the way down to neutral and acidic.

In compliance with the statute, this disclosure has been provided in language more or less specific as to structural and methodical features. It is to be understood, however, that the disclosure is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

The invention claimed is:

1. A hydrogenolysis process comprising:
providing a reactant mixture to a reactor to form a product mixture, the reactant mixture comprising a glycerol and a base, and the product mixture comprising propylene glycol, organic acids, and/or salts of organic acids, wherein the carbon molar selectivity to the organic acids and/or salts of organic acids is less than 2% and the carbon molar selectivity to the propylene glycol is at least 30%.

TABLE 7

| | Low acid | | | | | | | | | | |
|---|---|---|---|---|---|---|---|---|---|---|---|
| | F76-1 | F76-2 | F76-3 | F76-4 | F76-G5 | F76-6 | F76-7 | F76-8 | F76-9 | F76-10 | F76-11 |
| System Conditions | | | | | | | | | | | |
| F76 5% Ru + 1% Cd, 58959-85-1 | | | | | Not Glorified Grab See HPLC Folder | | | | | | |
| Hours on stream | 43:58:00 | 68:49:00 | 92:57:00 | 123:05:00 | | 216:28:00 | 260:34:00 | 284:12:00 | 308:11:00 | 380:35:00 | 404:38:00 |
| Cat. Bed Temp (° C.) | 190 | 190 | 190 | 190 | 190 | 190 | 190 | 190 | 190 | 185 | 210 |
| System Pressure | 1200 | 1200 | 1200 | 1200 | 1200 | 1200 | 1200 | 1200 | 1200 | 1200 | 1200 |
| Liq. Feed Rate (ml/hr) | 50 | 50 | 50 | 25 | 50 | 25 | 50 | 35 | 50 | 50 | 25 |
| Glycerol Feed Concentration (wt %) | 35.71 | 35.71 | 43.58 | 43.58 | 44.95 | 44.95 | 35.52 | 35.52 | 35.71 | 35.69 | 44.95 |
| Glycerol Source | ADM | ADM | ADM | ADM | ADM | ADM | ADM | ADM | ADM | ADM | ADM |
| NaOH Feed Concentration (wt %) | 2.10 | 2.10 | 0.50 | 0.50 | 0.00 | 0.00 | 1.00 | 1.00 | 2.10 | 2.10 | 0.00 |
| H2/Glycerol Molar Feed Ratio | 5 | 5 | 5 | 5 | 5 | 5 | 5 | 5 | 5 | 5 | 5 |
| H2 Flow Rate (SCCM) | 450 | 450 | 450 | 252 | 252 | 252 | 454 | 252 | 454 | 454 | 454 |
| % Wt. Recovery | 97.44 | 97.94 | 97.05 | 98.98 | | 92.12 | 96.81 | 96.49 | 98.62 | 98.38 | 97.76 |
| % Carbon Recovery | 96.46 | 94.70 | 99.02 | 99.58 | | 98.67 | 95.64 | 96.18 | 96.51 | 96.10 | 100.55 |
| Glycerol Conversion (By Difference) | 0.97 | 0.98 | 0.61 | 0.73 | | 0.13 | 0.86 | 0.91 | 0.94 | 0.96 | 0.31 |
| LHSV (cc feed/cc cat/h) | 1.67 | 1.67 | 1.67 | 0.83 | | 0.83 | 1.67 | 1.17 | 1.67 | 1.67 | 0.83 |
| WHSV (g/gly/g cat/h) | 1.35 | 1.35 | 1.65 | 0.83 | | 0.85 | 1.35 | 0.94 | 1.35 | 1.35 | 0.85 |
| Space Time Yield (g PG/cc cat/h) | 0.47 | 0.47 | 0.39 | 0.23 | | 0.04 | 0.42 | 0.31 | 0.46 | 0.47 | 0.11 |
| Selectivities | | | | | | | | | | | |
| PG C Molar Selectivity | 0.907 | 0.920 | 0.964 | 0.963 | | 0.990 | 0.947 | 0.941 | 0.915 | 0.928 | 0.991 |
| Lactate C Molar Selectivity | 0.029 | 0.031 | 0.007 | 0.008 | | 0.000 | 0.020 | 0.021 | 0.040 | 0.036 | 0.000 |
| EG C Molar Selectivity | 0.021 | 0.020 | 0.016 | 0.015 | | 0.010 | 0.017 | 0.016 | 0.016 | 0.015 | 0.009 |
| Formate C Molar Selectivity | 0.012 | 0.011 | 0.006 | 0.005 | | 0.000 | 0.006 | 0.006 | 0.008 | 0.007 | 0.000 |
| Glycerate C Molar Selectivity | 0.004 | 0.003 | 0.003 | 0.004 | | 0.000 | 0.006 | 0.006 | 0.006 | 0.007 | 0.000 |
| Methanol C molar Selectivity | 0.006 | 0.000 | 0.000 | 0.000 | | 0.000 | 0.000 | 0.004 | 0.000 | 0.000 | 0.000 |
| Ethanol C Molar Selectivity | 0.013 | 0.012 | 0.003 | 0.004 | | 0.000 | 0.004 | 0.005 | 0.008 | 0.004 | 0.000 |
| Propanol (1&2) C Molar Selectivity | 0.003 | 0.002 | 0.001 | 0.001 | | 0.000 | 0.001 | 0.001 | 0.003 | 0.001 | 0.000 |

2. The process of claim 1 wherein a weight ratio of the base to the glycerol is between 0.01 and 0.05.

3. The process of claim 1 wherein the base comprises from about 0.5% to about 2.1% of mixture.

4. The process of claim 1 wherein the base comprises less than about 1.0% of the reactant mixture.

5. The process of claim 1 wherein the base comprises from about 0.5% to about 1.0% of the reactant mixture.

6. The process of claim 1 wherein the reactant mixture further comprises a catalyst, and the catalyst comprises one or more of Zn, Cd, Se, Te, Cu, Re, and/or Sn.

7. The process of claim 1 wherein the reactant mixture further comprises a catalyst, and the catalyst comprises carbon.

8. The process of claim 1 wherein the reactant mixture further comprises water.

9. The process of claim 8 wherein the water is at least about 10% of the reactant mixture.

10. The process of claim 1 wherein the reactant mixture further comprises a reducing agent.

11. The process of claim 10 wherein the reducing agent comprises $H_2$.

12. A hydrogenolysis process comprising:
providing at least glycerol; and
hydrogenolyzing the glycerol to form propylene glycol, organic acids and/or salts of organic acids, wherein the carbon molar selectivity to organic acids and/or salts of organic acids is less than 2% and the carbon molar selectivity to propylene glycol is at least 30%.

13. The process of claim 12 further comprising hydrogenolyzing the glycerol in the presence of a base to form the propylene glycol.

14. The process of claim 13 wherein the base comprises Na and/or K.

15. The process of claim 14 wherein at least one of the salts of organic acids comprises lactate.

* * * * *